United States Patent [19]

Parg et al.

[11] Patent Number: 4,512,797
[45] Date of Patent: Apr. 23, 1985

[54] 1,3,5-TRIAZINONES AND THEIR USE FOR CONTROLLING UNDESIRABLE PLANT GROWTH

[75] Inventors: Adolf Parg, Bad Durkheim; Gerhard Hamprecht, Weinheim; Bruno Wuerzer, Otterstadt, all of Fed. Rep. of Germany

[73] Assignee: BASF Aktiengesellschaft, Fed. Rep. of Germany

[21] Appl. No.: 462,024

[22] Filed: Jan. 28, 1983

Related U.S. Application Data

[63] Continuation-in-part of Ser. No. 446,064, Dec. 1, 1982, abandoned.

[30] Foreign Application Priority Data

Dec. 3, 1981 [DE] Fed. Rep. of Germany ....... 3147879

[51] Int. Cl.³ .................... C07D 251/34; A01N 43/64
[52] U.S. Cl. ........................................ 71/93; 544/221; 544/222
[58] Field of Search ..................... 544/221, 222; 71/93

[56] References Cited

U.S. PATENT DOCUMENTS 4,219,552 8/1980 Haberkorn et al. ................ 544/221

Primary Examiner—John M. Ford
Attorney, Agent, or Firm—Keil & Weinkauf

[57] ABSTRACT

1,3,5-Triazinones of the formula

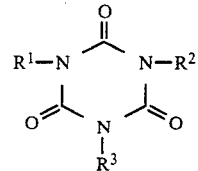

where $R^1$, $R^2$ and $R^3$ have the meanings given in the description, are used for controlling undesirable plant growth.

8 Claims, No Drawings

1,3,5-TRIAZINONES AND THEIR USE FOR CONTROLLING UNDESIRABLE PLANT GROWTH

This invention is a continuation-in-part of U.S. patent application Ser. No. 446,064, filed Dec. 1, 1982, now abandoned.

The present invention relates to 1,3,5-triazinones, herbicides containing these compounds as the active ingredients, and a method of controlling undesirable plant growth using these active ingredients.

German Laid-Open Application DOS No. 2,246,109 has disclosed the use of phenoxy-substituted N-phenyl-1,3,5-triazinones, such as 1-[4-(2'-chloro-4'-trifluoromethylphenoxy)-phenyl]-3-methyl-1,3,5-triazine 2,4,6-(1H,3H,5H)-trione, as drugs, especially as coccidiostatics.

We have found that 1,3,5-triazinones of the formula

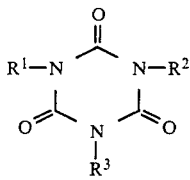

where $R^1$ is

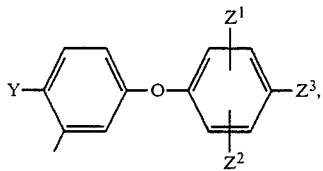

where $Z^1$ and $Z^2$ independently of one another are each hydrogen, halogen, nitro, cyano or carboxyl, or alkyl, haloalkyl or alkoxy, each of not more than 4 carbon atoms, $Z^3$ is halogen, nitro or cyano, or alkyl, haloalkyl, alkoxy, haloalkoxy, alkylmercapto, haloalkylmercapto, alkylsulfinyl, haloalkylsulfinyl, alkylsulfonyl or haloalkylsulfonyl, each of not more than 4 carbon atoms, and Y is hydrogen, halogen, cyano or nitro, and $R^2$ is hydrogen or a saturated or unsaturated, straight-chain or branched aliphatic radical of not more than 20 carbon atoms, or $R^2$ is a saturated, straight-chain or branched aliphatic radical of not more than 10 carbon atoms which is substituted by halogen, cyano, hydroxyl or mercapto, or by alkoxy or alkylmercapto, each of not more than 4 carbon atoms, or by phenylmercapto, or by alkylamino or dialkylamino, where each alkyl is of 1 to 4 carbon atoms, or $R^2$ is cycloalkyl of 3 to 7 carbon atoms which is unsubstituted or substituted by alkoxy of 1 to 4 carbon atoms, or $R^2$ is phenyl which is unsubstituted or substituted by halogen, or by alkyl or alkoxy, each of 1 to 4 carbon atoms, or by nitro or cyano, or by haloalkyl, haloalkoxy or haloalkylmercapto, each of 1 to 4 carbon atoms, or $R^2$ is benzyl or halobenzyl, and $R^3$ is hydrogen, alkyl of not more than 4 carbon atoms or acyl of not more than 7 carbon atoms which is unsubstituted or substituted by halogen, or is an alkali metal ion or an ammonium ion, which may be alkylated, have very good herbicidal properties and are selective in crops.

In formula I, if $R^1$ is

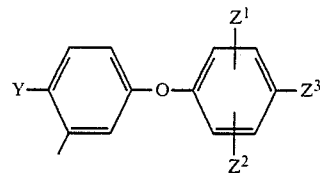

$Z^1$ and $Z^2$ independently of one another can each be, for example, hydrogen, halogen, such as fluorine, chlorine, bromine or iodine, nitro, cyano or carboxyl, or alkyl, haloalkyl or alkoxy, each of not more than 4 carbon atoms, eg. methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, ethoxy, n-propoxy, i-propoxy or tert.-butoxy, and $Z^3$ is halogen, such as fluorine, chlorine, bromine or iodine, or nitro or cyano, or alkyl, haloalkyl, alkoxy, haloalkoxy, alkylmercapto, haloalkylmercapto, alkylsulfinyl, haloalkylsulfinyl, alkylsulfonyl or haloalkylsulfonyl, each of not more than 4 carbon atoms, eg. methyl, ethyl, n-propyl, i-propyl, n-butyl, tert.-butyl, trifluoromethyl, difluoromethyl, fluoromethyl, trichloromethyl, dichloromethyl, chloromethyl, difluorochloromethyl, 1-chloroethyl, 2-chloroethyl, 1-fluoroethyl, 2-fluoroethyl, 2,2,2-trichloroethyl, 2,2,2-trifluoroethyl, 1,1,2,2-tetrafluoroethyl, 1,1,2-trifluoro-2-chloroethyl, 1,1,2,2,2-pentafluoroethyl, methoxy, n-propoxy, i-propoxy, tert.-butoxy, trichloromethoxy, trifluoromethoxy, 1-chloroethoxy, 2-chloroethoxy, 1-fluoroethoxy, 2-fluoroethoxy, 2,2,2-trichloroethoxy, 2,2,2-trifluoroethoxy, 1,1,2,2-tetrafluoroethoxy, 1,1,2,2,2-pentafluoroethoxy, methylmercapto, ethylmercapto, trichloromethylmercapto, trifluoromethylmercapto, methylsulfinyl, ethylsulfinyl, methylsulfonyl, ethylsulfonyl or trifluoromethylsulfonyl, and Y can be, for example, halogen, such as fluorine, chlorine, bromine or iodine, or hydrogen, cyano or nitro.

$R^2$ in formula I is hydrogen, or is a saturated or unsaturated, straight-chain or branched aliphatic radical of not more than 20 carbon atoms, for example alkyl of not more than 20 carbon atoms, preferably of not more than 12 and especially of not more than 4 carbon atoms, or alkenyl or alkynyl of not more than 20 carbon atoms, preferably of not more than 12 and especially of not more than 4 carbon atoms, eg. methyl, ethyl, n-propyl, isopropyl, n-butyl, isobutyl, sec.-butyl, tert.-butyl, n-pentyl, tert.-amyl, n-hexyl, pent-3-yl, 1,2-dimethyl-n-propyl, -1,3-dimethyl-n-butyl, 1-ethyl-2-methyl-n-propyl, 1,2,2-trimethyl-n-propyl, 1,2-dimethyl-4-hexyl, allyl, methallyl, crotyl, 2-ethyl-hex-2-enyl, hex-5-enyl, 2-methyl-but-2-enyl, 2-methyl-but-3-enyl, but-1-en-3-yl, 2-methyl-but-1-en-4-yl, 2-methyl-but-2-en-4-yl, 3-methyl-but-1-en-3-yl, propargyl, but-1-yn-3-yl or but-2-ynyl, or $R^2$ is a saturated, straight-chain or branched aliphatic radical of not more than 10 carbon atoms, preferably of not more than 4 carbon atoms, which is substituted by halogen, cyano, hydroxyl, mercapto or alkoxy of 1 to 4 carbon atoms, for example alkyl of not more than 10 carbon atoms, preferably of 1 to 4 carbon atoms, which is substituted by halogen, cyano, hydroxyl, mercapto or alkoxy of not more than 4 carbon atoms, eg. 2-chloroethyl, 2-chloro-n-propyl, 3-chloro-n-propyl, 2-chlorosec.-butyl, 2-chloro-isobutyl, 2-fluoro-sec.-butyl, 2-fluoro-isobutyl, 2-fluoro-isopropyl, chloro-tert.-butyl, 2,2,2-trifluoroethyl, 1-cyanomethyl, 2-cyanomethyl, 2-hydroxyethyl, 3-hydroxy-n-propyl, 2-mercapto-ethyl, 3-mercapto-n-propyl, 2-methoxyethyl, 2-ethoxyethyl, 3-methoxy-n-propyl, 2-methoxy-isopropyl, 3-methoxy-n-butyl, 1-methoxy-sec.-butyl, methoxy-tert.-butyl, ethoxy-tert.-butyl, 2-methoxy-n-butyl or 4-methoxy-n-butyl, or $R^2$ is cycloalkyl of 3 to 7 carbon atoms which is unsubstituted or substituted by alkoxy of 1 to 4 carbon atoms, eg. cyclopropyl, cyclopentyl, cyclohexyl or 4-ethoxycyclohexyl.

$R^2$ can also be a saturated, straight-chain or branched aliphatic radical of not more than 10 carbon atoms which is substituted by phenylmercapto, by alkylmercapto of not more than 4 carbon atoms, or by alkyl- or dialkylamino, where alkyl is of 1 to 4 carbon atoms, for example—alkyl of not more than 10 carbon atoms, preferably of 1 to 4 carbon atoms, which is substituted by phenylmercapto or alkylmercapto of 1 to 4 carbon atoms or by alkylamino or dialkylamino, which each alkyl is of 1 to 4 carbon atoms, eg. 2-methylmercapto-ethyl, 2-ethylmercapto-ethyl, 3-methylmercapto-n-propyl, 3-methylmercapto-n-butyl, 1-methylmercapto-sec.-butyl, methylmercapto-tert.-butyl, 2-methylmercapto-n-butyl, 2-methylaminoethyl, 2-ethylaminoethyl, 2-dimethylaminoethyl, 2-diethylaminoethyl, 2-dimethylamino-n-propyl, 3-dimethylamino-n-propyl or 4-dimethylamino-n-butyl, or $R^2$ is phenyl which is unsubstituted or substituted by halogen, or by alkyl or alkoxy of 1 to 4 carbon atoms, or by nitro or cyano, or by haloalkyl, haloalkoxy or haloalkylmercapto of 1 to 4 carbon atoms, or is benzyl or halobenzyl, eg. phenyl, 4-chlorophenyl, 3,4-dichlorophenyl, o-, m- or p-tert.-butylphenyl, o-, m- or p-methoxyphenyl, o-, m- or p-methylphenyl, 4-methoxy-3-chlorophenyl, 2-methyl-4-chlorophenyl, 4-nitrophenyl, 4-nitro-2-chlorophenyl, o-, m- or p-cyanophenyl, o- or m-trifluoromethylphenyl, 2-chloro-4-trifluoromethylphenyl, 4-trifluoromethoxyphenyl, 4-trifluoromethylmercaptophenyl, 3-trifluoromethylmercaptophenyl, benzyl, 2,6-dichlorobenzyl, 2-chloro-6-fluorobenzyl, 2,6-difluorobenzyl, or o-, m- or p-chlorobenzyl.

$R^3$ can be hydrogen, alkyl of not more than 4 carbon atoms, or acyl of not more than 7 carbon atoms, which may be substituted by halogen, or an alkali metal ion or an ammonium ion, which may be alkylated, eg. methyl, ethyl, n-propyl, isopropyl, n-butyl, 2-butyl, formyl, acetyl, chloroacetyl, benzoyl, sodium, potassium, ammonium, methylammonium, dimethylammonium, trimethylammonium or tetramethylammonium.

Preferred 1,3,5-triazinones are those compounds of the formula I where $R^1$ is

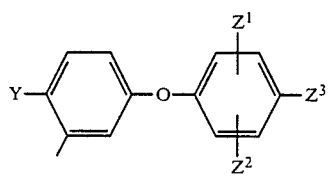

where $Z^1$ and $Z^2$ independently of one another are hydrogen, chlorine, bromine or cyano, $Z^3$ is chlorine, bromine, methyl, trifluoromethoxy, trifluoromethylmercapto or trifluoromethyl, preferably trifluoromethyl, and Y is bromine or nitro, in particular nitro, and $R^2$ is alkyl of 1 to 4 carbon atoms, which is unsubstituted or substituted by halogen, cyano, alkoxy or alkylmercapto, or is cycloalkyl of 3 to 7 carbon atoms, or is phenyl which is substituted by haloalkyl of 1 to 4 carbon atoms or by halogen, or is halobenzyl, preferably methyl, ethyl, 2-chloroethyl, 2-cyanoethyl, 2-methoxyethyl, 2-methylmercaptoethyl, cyclohexyl, 3,4-dichlorophenyl, 3-trifluoromethylphenyl or 4-chlorobenzyl, in particular methyl, 2-chloroethyl, 2-methoxyethyl or 3,4-dichlorophenyl, and $R^3$ is hydrogen, methyl or sodium.

The compounds of the formula I where $R^3$ is hydrogen can be prepared, for example, by the following process:

A phenoxy-substituted urea of the formula

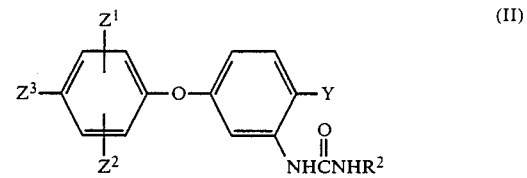

where $Z^1$, $Z^2$, $Z^3$, Y and $R^2$ have the above meanings, is reacted with a substituted carbonyl isocyanate of the formula

where $R^4$ is halogen, alkoxy or aryloxy, in an inert organic solvent, with or without addition of an acid acceptor, at from $-20°$ to $+180°$ C., preferably from $+20°$ to $+150°$ C., at atmospheric or superatmospheric pressure, continuously or batchwise, to give a substituted 1,3,5-triazinone of the formula

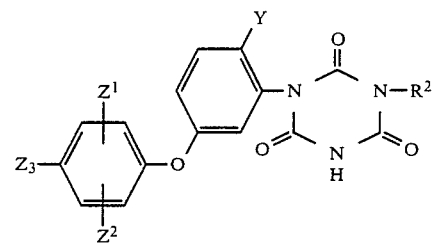

where $Z^1$, $Z^2$, $Z^3$, Y and $R^2$ have the above meanings.

If desired, this product can then be acylated or alkylated with an acyl halide of the formula $R^3COX$, an alkyl halide of the formula $R^3X$ or a dialkylsulfate of the formula $(R^3O)_2SO_2$, where $R^3$ in each case has the above meanings, with the exception of hydrogen, and X is halogen, or converted into a salt of the formula I with an alkali metal alcoholate, an alkali metal hydroxide, ammonium hydroxide or an alkylated ammonium hydroxide.

If N-3-(2'-chloro-4'-trifluoromethylphenoxy)-6-nitrophenyl-N'-methylurea and chlorocarbonylisocyanate are used as the starting substances and dimethylsulfate is used as the alkylating agent, the course of the reaction can be represented by the following equation:

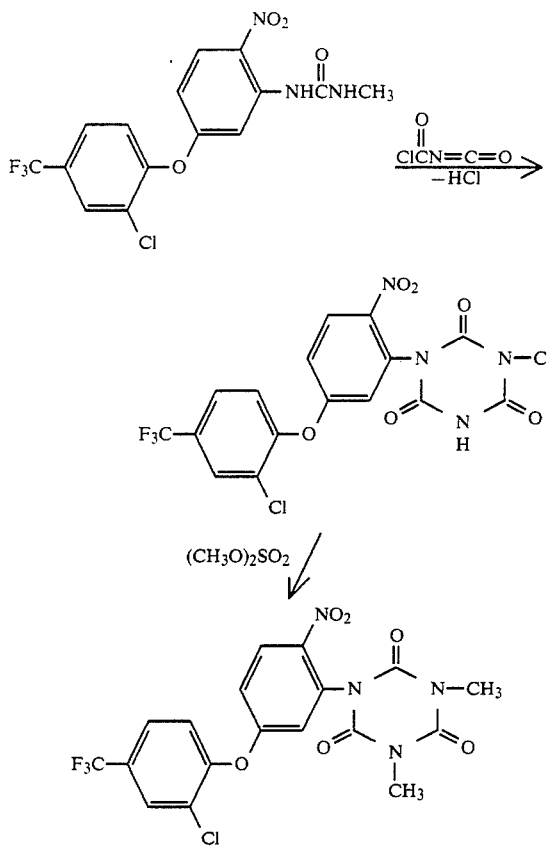

The reaction is carried out in organic solvents which are inert under the particular conditions, for example halohydrocarbons, in particular aromatic or aliphatic chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, m- or p-dibromobenzene, o-, m- or p-chlorotoluene or 1,2,4-trichlorobenzene, ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane or β,β'-dichlorodiethyl ether, nitrohydrocarbons, eg. nitromethane, nitroethane, nitrobenzene, o-, m- or p-chloronitrobenzene and o-nitrotoluene, nitriles, eg. acetonitrile, butyronitrile, isobutyronitrile, benzonitrile and m-chlorobenzonitrile, aliphatic or cycloaliphatic hydrocarbons, eg. heptane, pinane, nonane, o-, m- or p-cymene, gasoline fractions within a boiling point range of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane, esters, eg. ethyl acetate, ethyl acetoacetate and isobutyl acetate, amides, eg. formamide, methylformamide and dimethylformamide, and ketones, eg. acetone and methyl ethyl ketone, and appropriate mixtures. The solvent is advantageously used in an amount of from 100 to 2,000% by weight, preferably from 200 to 700% by weight, based on the starting substances.

The hydrochloric acid formed during the reaction escapes as a gas, or is bonded by acid acceptors. Any of the conventional acid acceptors can be used, preferably tertiary amines, alkaline earth metal compounds, ammonium compounds and alkali metal compounds or appropriate mixtures. Zinc compounds can also be used. Examples of suitable basic compounds are potassium hydroxide, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, diisopropylethylamine, trihexylamine, N,N-dimethylaniline, N,N-diethylaniline, N,N-dipropyltoluidine, N,N-dimethyl-p-aminopyridine, N-methylpyrrolidone, N-ethylpyrrolidone, N-methylpiperidine, N-ethylpiperidine, N-methyl-pyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

The starting substances are reacted in, for example, approximately the stoichiometric ratio, ie. starting substance III can be employed in, for example, an excess of not more than 20 mole%, based on II.

The process for the preparation of the compounds of the formula I is advantageously carried out by taking the starting substance II, if appropriate in one of the above diluents, and then adding the starting substance III and, where appropriate, an acid acceptor, at the same time or successively. However, it is also possible to take the starting substance III in a diluent and then to add the starting substance II and an acid acceptor by two separate lines, at the same time or in either order.

In many cases, the reaction has ended once the components have been brought together, otherwise the mixtures is stirred for a further period of from 10 minutes to 10 hours at from −20° to 180° C., preferably from 20° to 150° C. and in particular from 40° to 100° C., until the reaction has ended.

If an inert gas is used to remove the hydrogen halide, stirring is advantageously continued for from 0.2 to 10 hours at from 40° to 100° C.

The end product I is isolated from the reaction mixture in a conventional manner, for example after distilling off solvents or excess starting substance III or directly by filtration with suction. In this case, the residue which remains is washed with water or dilute alkali, to remove acid impurities, and dried. If water-immiscible diluents are used, the reaction mixture can also be extracted directly with water or with dilute alkali and the extract then dried and concentrated. However, it is also possible to dissolve the residue in a water-immiscible solvent and to wash the solution as described. The desired end products are thereby obtained in a pure form, and if necessary they can be purified by recrystallization, chromatography or distillation.

The compounds of the formula I where $R^3$ is alkyl, acyl, an alkali metal ion or an ammonium ion which may be alkylated can be prepared from the corresponding compounds of the formula I where $R^3$ is hydrogen, in a conventional manner. Alkylation is effected by means of alkylating agents, such as alkyl halides (eg. methyl bromide or ethyl iodide), dialkylsulfates (eg. dimethylsulfate or diethylsulfate) or oxonium salts (eg. trimethyloxoniumtetrafluoborate), in the presence or absence of an inert organic solvent and in the presence or absence of an acid acceptor, at from $-20°$ C. to $100°$ C., preferably from $0°$ to $100°$ C., under atmospheric or superatmospheric pressure, continuously or batchwise. Acylation is effected by means of acyl halides (eg. acetyl chloride or benzyl chloride), in the presence or absence of an inert organic solvent and in the presence or absence of an acid acceptor, at from $-20°$ C. to $150°$ C., preferably from $20°$ to $120°$ C., under atmospheric or superatmospheric pressure, continuously or batchwise.

To prepare a salt, a compound of the formula I where $R^3$ is hydrogen is advantageously dissolved in an organic solvent, eg. methanol, approximately the stoichiometric amount of alkali metal alcoholate, eg. sodium methylate, alkali metal hydroxide, eg. sodium hydroxide, ammonium hydroxide or alkylated ammonium hydroxide is added, and the mixture is concentrated to dryness.

The starting compounds can be prepared in a conventional manner. Thus, the phenoxy-substituted ureas of the formula II are prepared by, for example, the procedure described in German Laid-Open Application DOS No. 2,942,930. The compounds of the formula III can be prepared by methods disclosed in the literature (Angew. Chem. 89 (1977), 789).

The Examples which follow illustrate the preparation of the compounds of the formula I by the process described. Parts by weight bear the same relation to parts by volume as that of the kilogram to the liter.

EXAMPLE 1

A solution of 6.4 parts by weight of N-chlorocarbonyl isocyanate in 5 parts by volume of absolute toluene is added to a suspension of 19.5 parts by weight of N-3-(2'-chloro-4'-trifluoromethylphenoxy)-6-nitrophenyl-N'-methylurea in 25 parts by volume of absolute toluene. The reaction mixture is heated, and is then stirred under reflux for two hours. After cooling, n-pentane is added and the precipitate formed is filtered off with suction. 19 parts by weight (83% of theory) of 1-[3'-(2''-chloro-4''-trifluoromethylphenoxy)-6'-nitrophenyl]-3-methyl-1,3,5-triazine-2,4,6-(1H,3H,5H)-trione (compound No. 1) of melting point $208°-211°$ C. are obtained.

EXAMPLE 2

A solution of 8 parts by weight of compound No. 1 in 100 parts by volume of acetone is stirred under reflux with 2.4 parts by weight of potassium carbonate and 2.2 parts by weight of dimethylsulfate for two hours. The reaction mixture is filtered, the filtrate is evaporated under reduced pressure, and the residue is recrystallized from diisopropyl ether. 8 parts by weight (97% of theory) of 1-[3'-(2''-chloro-4''-trifluoromethylphenoxy)-6'-nitrophenyl]-3,5-dimethyl-1,3,5-triazine-2,4,6-(1H,3H,5H)-trione (compound No. 2) of melting point $200°-205°$ C. are obtained.

EXAMPLE 3

5 parts by weight of compound No. 1 are suspended in 50 parts by volume of absolute methanol, and 1.96 parts by weight of 30% strength methanolic sodium methylate solution are added. The mixture is stirred at room temperature for 30 minutes and is evaporated under reduced pressure. 5 parts by weight (99% of theory) of the sodium salt of 1-[3'-(2''-chloro-4''-trifluoromethylphenoxy)-6'-nitrophenyl]-3-methyl-1,3,5-triazine-2,4,6-(1H,3H,5H)-trione (compound No. 3) of melting point $220°-225°$ C. are obtained.

The compounds listed in the Table below are prepared in a manner similar to that in the above Examples.

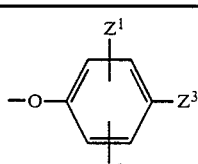

| No. | $Z^2$ | Y | $R^2$ | $R^3$ | M.p. [°C.]/$n_D^{25}$/ wavelength of a band in the infrared spectrum |
|---|---|---|---|---|---|
| 4 | 2-chloro-4-trifluoromethylphenyl | NO$_2$ | CH$_3$ | K | |
| 5 | ″ | ″ | C$_2$H$_5$ | H | |
| 6 | ″ | ″ | ″ | CH$_3$ | |
| 7 | ″ | ″ | ″ | Na | |
| 8 | ″ | ″ | ″ | C$_2$H$_5$ | |
| 9 | ″ | ″ | CH$_3$ | $\overset{O}{\overset{\|}{C}}$CH$_3$ | |
| 10 | ″ | ″ | ″ | $\overset{O}{\overset{\|}{C}}$C$_6$H$_5$ | |
| 11 | ″ | ″ | ″ | NH$_4^\oplus$ | |
| 12 | ″ | ″ | i-C$_3$H$_7$ | H | 218–220 |
| 13 | ″ | ″ | ″ | CH$_3$ | 150–155 |
| 14 | ″ | ″ | ″ | Na | |
| 15 | ″ | ″ | n-C$_6$H$_{13}$ | H | |
| 16 | ″ | ″ | ″ | CH$_3$ | |

4,512,797

-continued

![structure: phenyl ring with -O- substituent, Z¹, Z², Z³ positions]

| No. | Z² | Y | R² | R³ | M.p. [°C.]/$n_D^{25}$/ wavelength of a band in the infrared spectrum |
|---|---|---|---|---|---|
| 17 | " | " | " | Na | |
| 18 | " | " | CH₂—CH=CH₂ | H | |
| 19 | " | " | " | CH₃ | |
| 20 | " | " | " | Na | |
| 21 | " | " | CH₂CH₂Cl | H | |
| 22 | " | " | " | CH₃ | |
| 23 | " | " | " | Na | |
| 24 | " | " | CH₂CH₂F | H | |
| 25 | " | " | " | CH₃ | |
| 26 | " | " | " | Na | |
| 27 | " | " | CH₂CH₂CN | H | |
| 28 | " | " | " | CH₃ | |
| 29 | " | " | " | Na | |
| 30 | " | " | CH₂CH₂OH | H | |
| 31 | " | " | " | CH₃ | |
| 32 | " | " | " | Na | |
| 33 | " | " | CH₂CH₂SH | H | |
| 34 | " | " | " | CH₃ | |
| 35 | " | " | " | Na | |
| 36 | " | " | CH₂CH₂OCH₃ | H | 170 (decomposition) |
| 37 | " | " | " | CH₃ | C=O 1680–1700 |
| 38 | " | " | " | Na | 110–114 |
| 39 | " | " | CH₂CH₂OC₂H₅ | H | |
| 40 | " | " | CH(C₂H₅)CH₂OC₂H₅ | H | |
| 41 | " | " | " | CH₃ | |
| 42 | " | " | " | Na | |
| 43 | " | " | CH₂CH₂CH₂OC₄H₉ | H | 100–110 |
| 44 | " | " | " | CH₃ | C=O 1690–1710 |
| 45 | " | " | " | Na | 100–105 |
| 46 | " | " | CH₂CH₂CH₂OCH₂(CH₂)₁₁CH₃ | H | |
| 47 | " | " | " | CH₃ | |
| 48 | " | " | " | Na | |
| 49 | " | " | CH(CH₃)CH₂OCH₃ | H | 200–205 |
| 50 | " | " | " | CH₃ | 60–65 |
| 51 | " | " | " | Na | 168–173 |
| 52 | " | " | CH₂CH₂O—n-C₃H₇ | H | |
| 53 | " | " | " | CH₃ | |
| 54 | " | " | " | Na | |
| 55 | " | " | CH₂CH₂OCH₂CH₂OH | H | |
| 56 | " | " | " | Na | |
| 57 | " | " | CH₂CH₂SCH₃ | H | 170–174 |
| 58 | " | " | " | CH₃ | 60 |
| 59 | " | " | " | Na | |
| 60 | " | " | CH₂CH₂S—n-C₈H₁₇ | H | |
| 61 | " | " | " | CH₃ | |
| 62 | " | " | CH(CH₃)CH₂SCH₃ | H | |
| 63 | " | " | " | CH₃ | |
| 64 | " | " | " | Na | |
| 65 | " | " | C(CH₃)₂CH₂SC₂H₅ | H | |
| 66 | " | " | " | CH₃ | |
| 67 | " | " | CH₂CH₂CH₂SCH₃ | H | 105–110 |
| 68 | " | " | " | CH₃ | C=O 1690–1710 |
| 69 | " | " | " | Na | 115–120 |
| 70 | " | " | CH₂CH₂N(CH₃)₂ | H | |
| 71 | " | " | " | CH₃ | |
| 72 | " | " | " | Na | |
| 73 | " | " | 4-chlorophenyl | H | |
| 74 | " | " | " | CH₃ | |
| 75 | " | " | 3,4-dichlorophenyl | H | 95 (decomposition) |
| 76 | " | " | " | CH₃ | C=O 1690–1720 |
| 77 | " | " | 3-trifluoromethylphenyl | H | 145 (decomposition) |
| 78 | " | " | " | CH₃ | C=O 1690–1710 |
| 79 | " | " | 4-trifluoromethoxyphenyl | H | |
| 80 | " | " | " | CH₃ | |
| 81 | " | " | 3-trifluoromethyl-mercaptophenyl | H | |
| 82 | " | " | 3-trifluoromethyl-mercaptophenyl | CH₃ | |
| 83 | " | " | 4-chlorobenzyl | H | |
| 84 | " | " | " | CH₃ | |
| 85 | " | " | 2,4-dichlorobenzyl | H | |

-continued

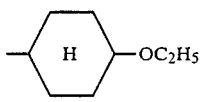

| No. | Z² | Y | R² | R³ | M.p. [°C.]/$n_D^{25}$/wavelength of a band in the infrared spectrum |
|---|---|---|---|---|---|
| 86 | " | " | " | CH₃ | |
| 87 | " | " | 4-methylbenzyl | H | |
| 88 | " | " | " | CH₃ | |
| 89 | " | " | cyclopentyl | H | 160–166 |
| 90 | " | " | " | CH₃ | C=O 1700–1710 |
| 91 | " | " | " | Na | 125–130 |
| 92 | " | " | cyclohexyl | H | 176–182 |
| 93 | " | " | " | CH₃ | 60–65 |
| 94 | " | " | " | Na | 131–136 |
| 95 | " | Br | CH₃ | H | |
| 96 | " | " | " | CH₃ | |
| 97 | " | " | " | Na | |
| 98 | " | " | CH₂CH₂OCH₃ | H | |
| 99 | " | " | " | CH₃ | |
| 100 | " | " | " | Na | |
| 101 | " | CN | CH₃ | H | |
| 102 | " | " | " | CH₃ | |
| 103 | 2-bromo-trifluormethylphenyl | NO₂ | CH₃ | H | |
| 104 | " | " | " | CH₃ | |
| 105 | " | " | " | Na | |
| 106 | 2,6-dichloro-4-trifluoro-methylphenyl | " | " | H | |
| 107 | 2,6-dichloro-4-trifluoro-methylphenyl | " | " | CH₃ | |
| 108 | 2,6-dichloro-4-trifluoro-methylphenyl | " | " | Na | |
| 109 | 2-chloro-4-trifluoro-methoxyphenyl | " | " | H | |
| 110 | 2-chloro-4-trifluoro-methoxyphenyl | " | " | CH₃ | |
| 111 | 2-chloro-4-trifluoro-methylmercapto-phenyl | " | " | H | |
| 112 | 2-chloro-4-trifluoro-methylmercapto-phenyl | " | " | CH₃ | |
| 113 | 2,4-dichlorophenyl | " | " | H | 224–229 |
| 114 | " | " | " | CH₃ | |
| 115 | 2,6-dibromophenyl | " | " | H | 223–225 |
| 116 | " | " | " | CH₃ | |
| 117 | " | " | " | Na | |
| 118 | 2,4,6-trichlorophenyl | " | " | H | |
| 119 | 3-chloro-4-trifluoromethylphenyl | " | " | H | |
| 120 | " | " | CH₂CH₂OCH₃ | H | |
| 121 | " | " | " | CH₃ | |
| 122 | 2-bromo-4-trifluoromethylphenyl | " | " | H | 170–175 |
| 123 | " | " | " | CH₃ | 1.5403 |
| 124 | " | " | " | Na | 135–145 |
| 125 | 2-chloro-4-fluorophenyl | " | " | H | |
| 126 | " | " | " | CH₃ | |
| 127 | 2-chloro-4-methylphenyl | " | " | H | |
| 128 | " | " | " | CH₃ | |
| 129 | 2-chloro-4-trifluoromethylphenyl | " | CH₂CH₂S—C₆H₅ | H | 217–222 |
| 130 | " | " | " | CH₃ | 55–61 |
| 131 | " | " | " | Na | 111–125 |
| 132 | " | " | " | C₂H₅ | 1.5732 |
| 133 | " | " | ⌬H—OC₂H₅ | H | 155 (decomposition) |
| 134 | " | " | " | CH₃ | 1.5146 |
| 135 | " | " | " | C₂H₅ | 1.5385 |
| 136 | " | " | " | Na | 140 (decomposition) |
| 137 | " | " | CH₂CH₂OCH₃ | C₂H₅ | 122–126 |
| 138 | " | " | (CH₂)₃OC₄H₉ | C₂H₅ | 1.5325 |
| 139 | " | " | cyclopentyl | C₂H₅ | 1.5468 |
| 140 | " | " | cyclohexyl | C₂H₅ | 1.5298 |
| 141 | " | " | (CH₂)₃S—CH₃ | C₂H₅ | 1.5597 |
| 142 | 2-bromo-4-trifluoromethylphenyl | " | CH₂CH₂OCH₃ | C₂H₅ | |
| 143 | 2,4-dichlorophenyl | " | " | H | C=O 1700–1710 |
| 144 | " | " | " | CH₃ | C=O 1700–1715 |
| 145 | " | " | " | C₂H₅ | 1.5744 |

-continued

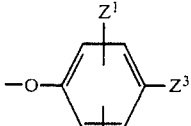

| No. | $Z^2$ | Y | $R^2$ | $R^3$ | M.p. [°C.]/$n_D^{25}$/ wavelength of a band in the infrared spectrum |
| --- | --- | --- | --- | --- | --- |
| 146 | " | " | " | Na | 122–128 |
| 147 | 2,4-dibromophenyl | " | " | H | 84–90 |
| 148 | " | " | " | $CH_3$ | 1.5631 |

The compounds of the formula I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 38 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 3 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 3 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 37 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 3 parts by weight of compound no. 36 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 146 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal agents may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year and the growth stage of the plants, and varies from 0.025 to 10 kg/ha and more, but is preferably from 0.1 to 4 kg/ha. The higher application rates are particularly suitable for total elimination of vegetation.

The herbicidal action of compounds of the formula I or herbicidal agents containing them is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The rice plants used for the postemergence treatment were grown in a peat-enriched substrate. Peat was also added to the soybeans to ensure better growth than in the abovementioned soil. For this treatment, either plants which had been sown directly in the pots and grown there were selected, or plants which had been grown separately as seedlings and transplanted to the experiment vessels a few days before treatment.

The pots were set up in the greenhouse—species from warmer areas at from 20° to 35° C., and species from moderate climates at 15° to 25° C. The experiments were run for from 3 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The test plants employed were *Abutilon theophrasti, Amaranthus spp., Arachis hypogaea, Chenopodium album, Datura stramonium, Echinochloa crus-galli, Galeopsis tetrahit*, Glycine max., *Oryza sativa, Sesbania exaltata, Sida spinosa, Sinapis alba, Solanum nigrum, Triticum aestivum*, and *Zea mays*.

The prior art compound used for comparison purposes was 1-[4'-(2''-chloro-4''-trifluoromethyl-phenoxy)-phenyl]-3-methyl-1,3,-5-triazine-2,4,6-trione (German Laid-Open Application DE-OS No. 22 46 109).

The results of the greenhouse experiments reveal that for instance compounds nos. 1, 36 and 37, applied preemergence at a rate of, for example, 3.0 kg/ha, have a good herbicidal action.

On investigations into selective herbicidal properties on postemergence application, compound no. 4, at 0.5 kg/ha, proves to have a better action on the broadleaved weed Chenopodium than the comparative agent, without damaging soybean and Indian corn plants.

For instance compounds nos. 1, 3, 36, 37, 38, 44, 45, 69, 90, 93, 146 and 148, applied postemergence at rates of 0.06, 0.125, 0.25 and 0.5 kg/ha, combat a number of unwanted broadleaved plants, depending on the active ingredient, in crops such as rice, wheat and groundnuts.

In view of the good tolerance of the active ingredients and the many application methods possible, the compounds according to the invention may be used in a large number of crop plants for removing unwanted plant growth.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rape seed |
| *Brassica napus* var. napobrassica | |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |

| Botanical name | Common name |
| --- | --- |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds according to the invention may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the agents according to the invention, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A 1,3,5-triazinone of the formula

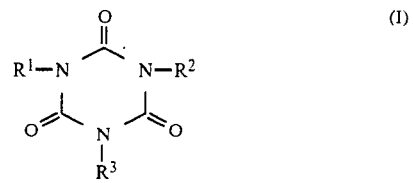

where $R^1$ is

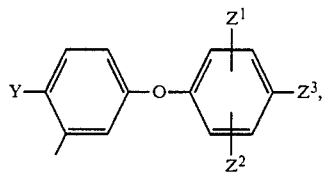

where $Z^1$ and $Z^2$ independently of one another are each hydrogen, halogen, nitro, cyano or carboxyl, or alkyl, haloalkyl or alkoxy, each of not more than 4 carbon atoms, $Z^3$ is halogen, nitro or cyano, or alkyl, haloalkyl, alkoxy, haloalkoxy, alkylmercapto, alkylsulfinyl, or alkylsulfonyl, each of not more than 4 carbon atoms, and Y is hydrogen, halogen, cyano or nitro, and $R^2$ is hydrogen or a saturated or unsaturated, straight-chain or branched aliphatic radical of not more than 20 carbon atoms, or $R^2$ is a saturated, straight-chain or branched aliphatic radical of not more than 10 carbon atoms which is substituted by halogen, cyano, hydroxyl or mercapto, or by alkoxy or alkylmercapto, each of not more than 4 carbon atoms, or by phenylmercapto, or by alkylamino or dialkylamino, where each alkyl is of 1 to 4 carbon atoms, or $R^2$ is cycloalkyl of 3 to 7 carbon atoms which is unsubstituted or substituted by alkoxy of 1 to 4 carbon atoms, or $R^2$ is phenyl which is unsubstituted or substituted by halogen, or by alkyl or alkoxy, each of 1 to 4 carbon atoms, or by nitro or cyano, or by haloalkyl, haloalkoxy or haloalkylmercapto, each of 1 to 4 carbon atoms, or $R^2$ is benzyl or halobenzyl, and $R^3$ is hydrogen, alkyl of not more than 4 carbon atoms or acyl of not more than 7 carbon atoms which is unsubstituted or substituted by halogen, or is an alkali metal ion or an ammonium ion or an alkylated ammonium ion.

2. A 1,3,5-triazinone of the formula I as defined in claim 1, where $R^1$ is

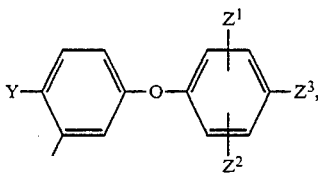

where $Z^1$ and $Z^2$ independently of one another are each hydrogen, chlorine, bromine or cyano, $Z^3$ is chlorine, bromine, methyl, trifluoromethoxy or trifluoromethyl and Y is bromine or nitro, $R^2$ is alkyl, haloalkyl, cyanoalkyl, alkoxy- or alkylmercaptoalkyl, each of not more than 4 carbon atoms, cycloalkyl of 3 to 7 carbon atoms, phenyl substituted by haloalkyl of 1 to 4 carbon atoms or by halogen, or benzyl substituted by halogen, and $R^3$ is hydrogen, methyl or sodium.

3. A 1,3,5-triazinone of the formula I as defined in claim 1, where $R^1$ is

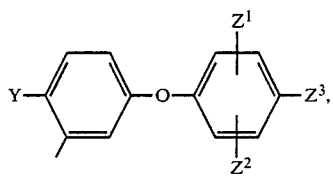

where $Z^1$ and $Z^2$ independently of one another are each hydrogen, chlorine, bromine or cyano, $Z^3$ is chlorine, bromine, methyl, trifluoromethoxy or trifluoromethyl, and Y is nitro, $R^2$ is methyl, 2-chloroethyl, 3,4-dichlorophenyl or 2-methoxyethyl, and $R^3$ is hydrogen, methyl or sodium.

4. 1-[3'-(2''-Chloro-4''-trifluoromethylphenoxy)-6'-nitrophenyl]-3-methyl-1,3,5-triazine-2,4,6-(1H,3H,5H)-trione.

5. A herbicide containing inert additives and a herbicidally effective amount of a 1,3,5-triazinone of the formula I as claimed in claim 1.

6. A herbicide containing inert additives and a herbicidally effective amount of a 1,3,5-triazinone of the formula I as claimed in claim 1, where $R^1$ is

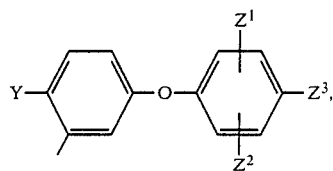

where $Z^1$ and $Z^2$ independently of one another are each hydrogen, chlorine, bromine or cyano, $Z^3$ is chlorine, bromine, methyl, trifluoromethoxy or trifluoromethyl and Y is bromine or nitro, $R^2$ is alkyl, haloalkyl, cyanoalkyl, alkoxy- or alkylmercaptoalkyl, each of not more than 4 carbon atoms, cycloalkyl of 3 to 7 carbon atoms, phenyl substituted by haloalkyl of 1 to 4 carbon atoms or by halogen, or benzyl substituted by halogen, and $R^3$ is hydrogen, methyl or sodium.

7. A herbicide containing inert additives and a herbicidally effective amount of a 1,3,5-triazinone of the formula I as claimed in claim 1, where $R^1$ is

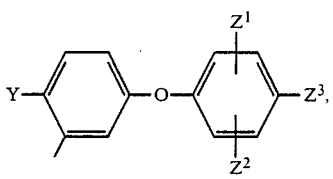

where $Z^1$ and $Z^2$ independently of one another are each hydrogen, chlorine, bromine or cyano, $Z^3$ is chlorine, bromine, methyl, trifluoromethoxy, trifluoromethylmercapto or trifluoromethyl, and Y is nitro, $R^2$ is methyl, 2-chloroethyl, 3,4-dichlorophenyl or 2-methoxyethyl, and $R^3$ is hydrogen, methyl or sodium.

8. A process for controlling unwanted plant growth, wherein the unwanted plants and/or the area to be kept free from unwanted plant growth are treated with a herbicidally effective amount of a 1,3,5-triazinone of the formula I as claimed in claim 1.

* * * * *

UNITED STATES PATENT AND TRADEMARK OFFICE
CERTIFICATE OF CORRECTION

PATENT NO. : 4,512,797
DATED : April 23, 1985
INVENTOR(S) : Adolf PARG et al.

It is certified that error appears in the above-identified patent and that said Letters Patent is hereby corrected as shown below:

Claim 7, lines 33 and 34, delete "trifluoromethylmercapto".

Signed and Sealed this

Tenth Day of September 1985

[SEAL]

Attest:

DONALD J. QUIGG

Attesting Officer   Acting Commissioner of Patents and Trademarks - Designate